Figure 1:
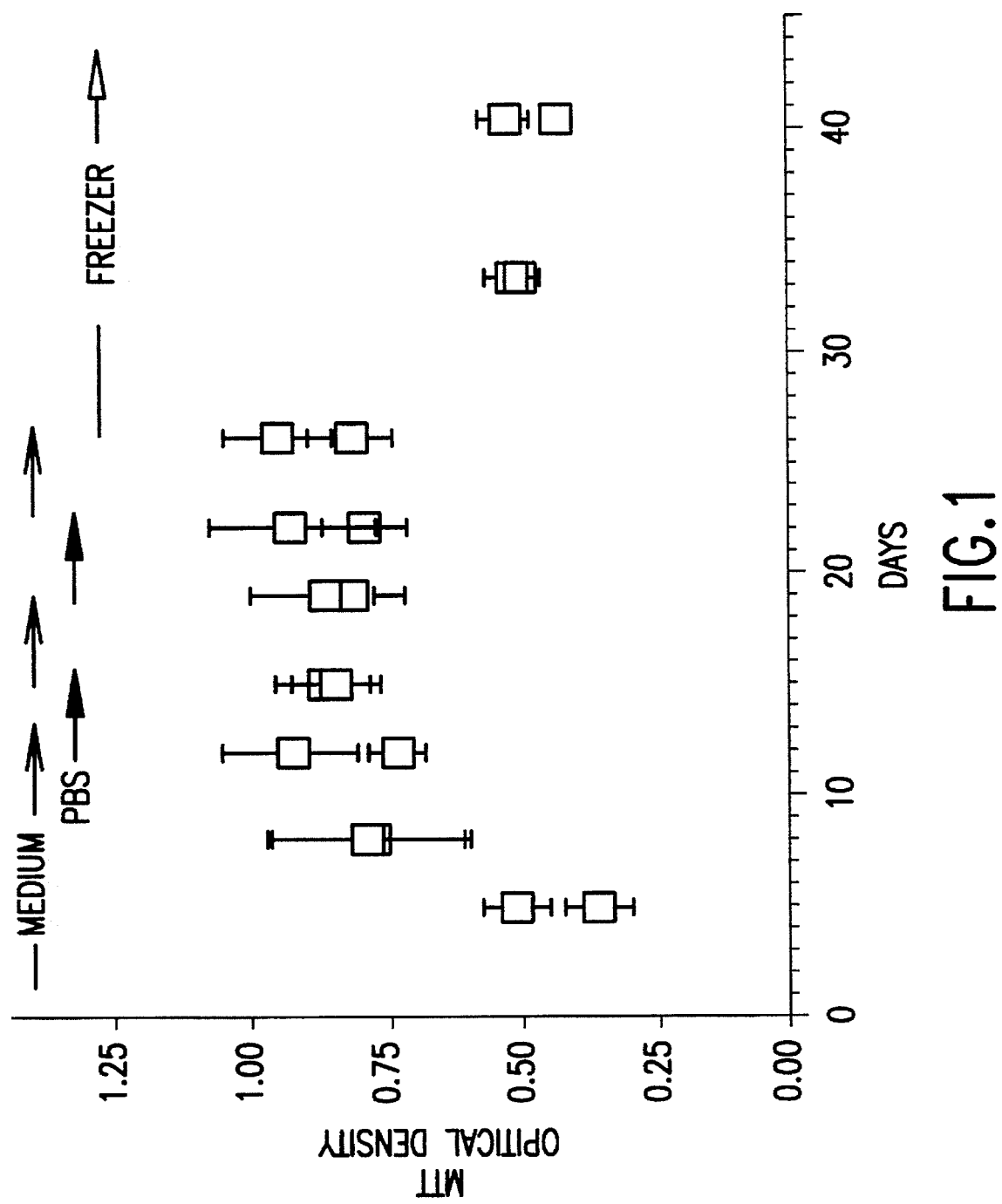

United States Patent [19]

Slivka et al.

[11] Patent Number: 5,478,739
[45] Date of Patent: Dec. 26, 1995

[54] THREE-DIMENSIONAL STROMAL CELL AND TISSUE CULTURE SYSTEM

[75] Inventors: Sandra R. Slivka; Lee Landeen, both of San Diego, Calif.

[73] Assignee: Advanced Tissue Sciences, Inc., La Jolla, Calif.

[21] Appl. No.: 965,476

[22] Filed: Oct. 23, 1992

[51] Int. Cl.⁶ .............................. C12N 5/00; A61F 2/10
[52] U.S. Cl. .................. 435/240.23; 435/240.2; 435/240.241; 435/240.243; 623/15
[58] Field of Search ............ 435/240.2, 240.23, 435/240.243, 240.3, 240.31, 240.21, 1; 623/15

[56] References Cited

U.S. PATENT DOCUMENTS

| | | | |
|---|---|---|---|
| 4,016,036 | 4/1977 | Green et al. | 435/240.23 |
| 4,721,096 | 1/1988 | Naughton et al. | 435/240.23 |
| 4,835,102 | 5/1989 | Bell et al. | 435/1 |
| 4,902,295 | 2/1990 | Walthall et al. | 623/11 |
| 4,963,489 | 10/1990 | Naughton et al. | 435/240.23 |
| 5,032,508 | 7/1991 | Naughton et al. | 435/240.23 |
| 5,153,132 | 10/1992 | Goodwin et al. | 435/240.24 |
| 5,155,034 | 10/1992 | Wolf et al. | 435/240.24 |
| 5,160,490 | 11/1992 | Naughton et al. | 435/1 |
| 5,198,356 | 3/1993 | Lieberman et al. | 435/240.2 |

OTHER PUBLICATIONS

Slivka et al, J. Cell Biol., 115 (3 Part 2), 1991, 357A.
Slivka et al, J. Cell Biol., 115 (3 Part 2), 1991, 236A.

*Primary Examiner*—Marian C. Knode
*Assistant Examiner*—Susan M. Dadio
*Attorney, Agent, or Firm*—Pennie & Edmonds

[57] ABSTRACT

The present invention relates to an improved three-dimensional cell culture system in which cells are grown on a three-dimensional matrix while cycling the cultures between metabolically favorable and metabolically unfavorable (but noncytotoxic) conditions. The invention is based, at least in part, on the discovery that cycling the cultures in this manner optimizes the formation of extracellular matrix and produces an overall structure that more closely resembles naturally occurring tissue.

14 Claims, 8 Drawing Sheets

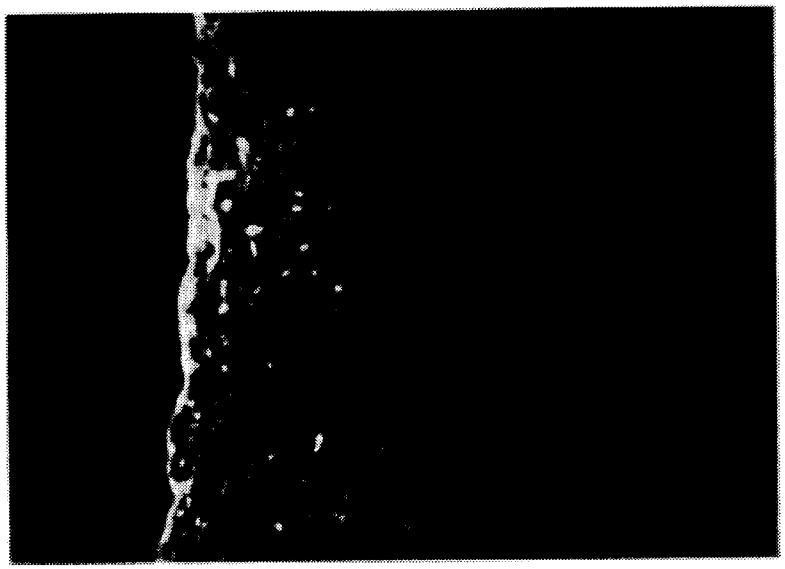
FIG. 7C HSPG 400x
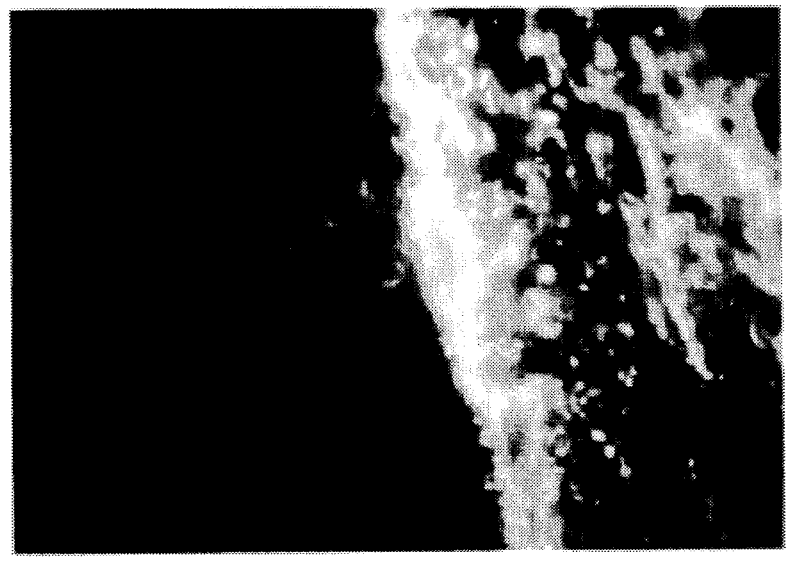
FIG. 7B Collagen Type IV 1000x
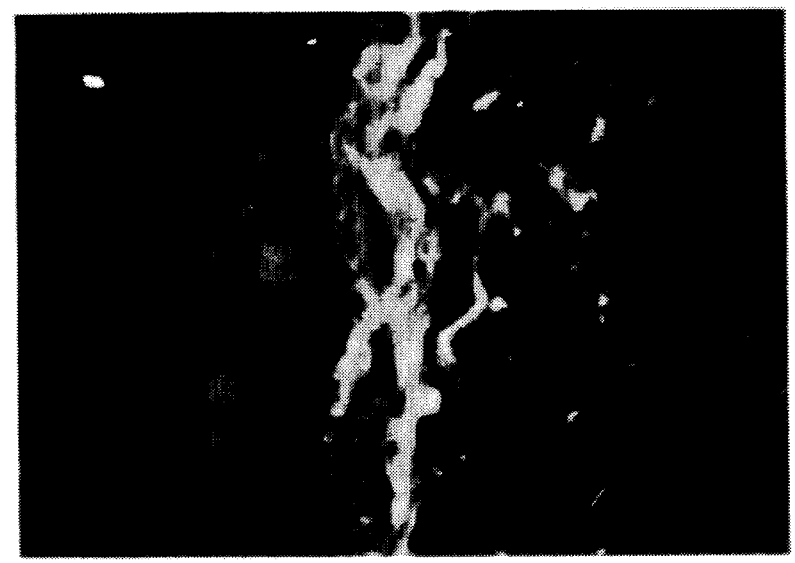
FIG. 7A Laminin 1000x

THREE-DIMENSIONAL STROMAL CELL AND TISSUE CULTURE SYSTEM

TABLE OF CONTENTS

1. INTRODUCTION
2. BACKGROUND OF THE INVENTION
3. SUMMARY OF THE INVENTION
   3.1. DEFINITIONS AND ABBREVIATIONS
4. DESCRIPTION OF THE FIGURES
5. DETAILED DESCRIPTION OF THE INVENTION
   5.1. ESTABLISHMENT OF THREE-DIMENSIONAL STROMAL MATRIX
   5.2. INOCULATION OF TISSUE-SPECIFIC CELLS ONTO THREE-DIMENSIONAL STROMAL MATRIX AND MAINTENANCE OF CULTURES
   5.3. USES OF THE THREE-DIMENSIONAL CULTURE SYSTEM
6. EXAMPLE: KERATINOCYTE/DERMAL CO-CULTURE
   6.1. MATERIALS AND METHODS
      6.1.1. CELL CULTURE OF THE DERMAL EQUIVALENT
      6.1.2. PREPARATION OF THE KERATINOCYTE/DERMAL EQUIVALENT CO-CULTURE
      6.1.3. HISTOLOGY, IMMUNOHISTOCHEMISTRY AND IMMUNOFLUORESCENCE
      6.1.4. IMMUNOBLOT ANALYSIS FOR FIBRONECTIN
      6.1.5. ANILINE BLUE ASSAY, MTT ASSAY, AND NUCLEAR COUNTS
      6.1.6. ELECTRON MICROSCOPY
   6.2. RESULTS
      6.2.1. OPTIMIZATION OF THE DERMAL MODEL FOR KERATINOCYTE GROWTH
      6.2.2. DERMAL MODEL ECM WAS SIMILAR TO FETAL/NEONATAL DERMIS ECM
      6.2.3. KERATINOCYTES MODULATE DERMAL EQUIVALENT ECM
   6.3. DISCUSSION

1. INTRODUCTION

The present invention is directed to an improved in vitro three-dimensional stromal cell and tissue culture system which produces tissue equivalents that more closely resemble naturally occurring structures and that may be used for the long term proliferation of cells. These tissue equivalents have a variety of applications ranging from transplantation or implantation in vivo to screening cytotoxic compounds and pharmaceutical compounds in vitro and to the production of biologically active molecules in bioreactors.

2. BACKGROUND OF THE INVENTION

The majority of vertebrate cell cultures in vitro are grown as two-dimensional monolayers on an artificial substrate bathed in nutrient medium. The nature of the substrate on which the monolayers grow may be solid, such as plastic, or semisolid gels, such as collagen or agar. Disposable plastics have become the preferred substrate used in modern-day tissue or cell culture.

While the growth of cells in two dimensions is a convenient method for preparing, observing and studying cells in culture, allowing a high rate of cell proliferation, it lacks the cell-cell and cell-matrix interactions characteristic of whole tissue in vivo. In order to study such functional and morphological interactions, a few investigators have explored the use of three-dimensional substrates such as collagen gel (Douglas et al., 1980, In Vitro 16:306–312; Yang et al., 1979, *Proc. Natl. Acad. Sci.* 76:3401; Yang et al., 1980, *Proc. Natl. Acad. Sci.* 77:2088–2092; Yang et al., 1981, *Cancer Res.* 41:1021–1027); cellulose sponge, alone (Leighton et al., 1951, *J. Natl. Cancer Inst.* 12:545–561) or collagen coated (Leighton et al., 1968, *Cancer Res.* 28:286–296); or a gelatin sponge, Gelfoam (Sorour et al., 1975, *J. Neurosurg.* 43:742–749).

In general, these three-dimensional substrates are inoculated with the cells to be cultured. Many of the cell types have been reported to penetrate the matrix and establish a "tissue-like" histology. For example, three-dimensional collagen gels have been utilized to culture breast epithelium (Yang et al., 1981, *Cancer Res.* 41:1021–1027) and sympathetic neurons (Ebendal, 1976, *Exp. Cell Res.* 98:159–169). Additionally, various attempts have been made to regenerate tissue-like architecture from dispersed monolayer cultures. Kruse and Miedema (1965, *J. Cell Biol.* 27:273) reported that perfused monolayers could grow to more than ten cells deep and organoid structures can develop in multilayered cultures if kept supplied with appropriate medium (see also Schneider et al., 1963, *Exp. Cell Res.* 30:449–459 and Bell et al., 1979, *Proc. Natl. Acad. Sci. USA* 76:1274–1279); Green (1978, *Science* 200:1385–1388) has reported that human epidermal kerotinocytes may form dematoglyphs (friction ridges) if kept for several weeks without transfer; Folkman and Haudenschild (1980, *Nature* 288:551–556) reported the formation of capillary tubules in cultures of vascular endothelial cells cultured in the presence of endothelial growth factor and medium conditioned by tumor cells; and Sirica et al. (1979, *Proc. Natl. Acad. Sci. U.S.A.* 76:283–287; 1980, *Cancer Res.* 40:3259–3267) maintained hepatocytes in primary culture for about 10–13 days on nylon meshes coated with a thin layer of collagen. However, the long term culture and proliferation of cells in such systems has not been achieved.

Indeed, the establishment of long term culture of tissues such as bone marrow had been attempted, but, overall, the results were disappointing, in that although a stromal cell layer containing different cell types was rapidly formed, significant hematopoiesis could not be maintained for any protracted period of time. (For review see Dexter et al., *In Long Term Bone Marrow Culture*, 1984, Alan R. Liss, Inc., pp.57–96).

U.S. Pat. No. 4,721,096, issued Jan. 26, 1988, and 5,032,508, issued Jul. 16, 1991, both by Naughton et al., disclose a three-dimensional cell culture system which, for the first time, achieves long-term proliferation of cells, including skin and bone marrow, as well as other tissues. Using this system, a living stromal tissue is prepared in vitro by allowing stromal cells and the connective tissue proteins they naturally secrete to attach to and substantially envelop a framework composed of a biocompatible, non-living material formed into a three-dimensional structure having interstitial spaces. The stromal cells bridge the interstitial spaces of the framework, thereby creating a living cellular matrix on which may be seeded parenchymal cells such as hematopoietic cells, hepatocytes, melanocytes, keratinocytes, etc. The resulting cultures give rise to "tissue equivalents" which functionally and histologically resemble naturally occurring tissues. The present invention constitutes an improvement of the three-dimensional cell and tissue culture system described in U.S. Pat. No. 4,721,096 and 5,032,508, both of which are incorporated by reference herein in their entirety.

3. SUMMARY OF THE INVENTION

The present invention relates to an improved three-dimensional cell culture system in which cells are grown on a three-dimensional matrix while cycling the cultures between metabolically favorable and metabolically unfavorable (but noncytotoxic) conditions. The invention is based, at least in part, on the discovery that cycling the cultures in this manner optimizes the formation of extracellular matrix and produces an overall structure that more closely resembles naturally occurring tissue.

According to the invention, stromal cells, which are fibroblasts with or without other cells and/or elements found in loose connective tissue, including endothelial cells, macrophages/monocytes, adiposites, pericytes, reticular cells found in bone marrow stroma, etc., are seeded onto a framework composed of a biocompatible, non-living material formed into a three-dimensional structure having interstitial spaces, such as, for example, a nylon mesh. The resulting cultures are then allowed to grow under metabolically favorable conditions for between about 3–6 cell cycles. The cultures are then allowed to "rest", under conditions which are not cytotoxic but which are metabolically unfavorable for between about 1–2 cell cycles. Thereafter, cultures are cycled between metabolically favorable conditions for 3–4 cell cycles and metabolically unfavorable conditions for 1–2 cell cycles until the desired level of extracellular matrix material is attained. Finally, parenchymal cells may be seeded onto the living matrix created by the stromal cells and their secretions. In specific embodiments of the invention, bone marrow, skin, liver, pancreas, mucosal epithelium, adenocarcinoma and melanoma tissues may be grown in the three-dimensional culture system.

Tissue equivalents produced by this improved three-dimensional culture system have a variety of applications ranging from transplantation or implantation in vivo to cytotoxicity testing and screening compounds in vitro, as well as serving as "bioreactors" for the production of biological materials.

3.1. DEFINITIONS AND ABBREVIATIONS

The following terms used herein shall have the meanings indicated:

Adherent Layer: cells attached directly to the three-dimensional matrix or connected indirectly by attachment to cells that are themselves attached directly to the matrix.

Stromal Cells: fibroblasts with or without other cells and/or elements found in loose connective tissue, including but not limited to, endothelial cells, pericytes, macrophages, monocytes, plasma cells, mast cells, adipocytes, etc.

Tissue-Specific or Parenchymal Cells: the cells which form the essential and distinctive tissue of an organ as distinguished from its supportive framework.

Three-Dimensional Matrix: a three-dimensional matrix composed of any material and/or shape that (a) allows cells to attach to it (or can be modified to allow cells to attach to it); and (b) allows cells to grow in more than one layer. This support is inoculated with stromal cells to form the three-dimensional stromal matrix.

Three-Dimensional Stromal Matrix: a three-dimensional matrix which has been inoculated with stromal cells. Whether confluent or subconfluent, stromal cells according to the invention continue to grow and divide. The stromal matrix will support the growth of tissue-specific cells later inoculated to form the three-dimensional cell culture.

Three-Dimensional Cell Culture: a three-dimensional stromal matrix which has been inoculated with tissue specific cells and cultured. In general, the tissue specific cells used to inoculate the three-dimensional stromal matrix should include the "stem" cells (or "reserve" cells) for that tissue; i.e., those cells which generate new cells that will mature into the specialized cells that form the parenchyma of the tissue.

The following abbreviations shall have the meanings indicated: DMEM=Dulbecco's Modified Eagle's Medium EDTA=ethylene diamine tetraacetic acid FBS=fetal bovine serum HBSS=Hank's balanced salt solution HS=horse serum LTBMC=long term bone marrow culture MEM= minimal essential medium PBL=peripheral blood leukocytes PBS=phosphate buffered saline RPMI 1640=Roswell Park Memorial Institute medium number 1640 (GIBCO, Inc., Grand Island, N.Y.) SEM=scanning electron microscopy

4. DESCRIPTION OF THE FIGURES

FIG. 1. Development of the Dermal Equivalent. Fibroblasts were seeded onto nylon mesh. The periods in (i) growth medium containing ascorbic acid, (ii) cold PBS, and (iii) freezer are shown. At the indicated days after seeding, fibroblast viability was evaluated by mitochondrial activity (MTT Assay). MTT reduction (O.D.) per 1.21 $cm^2$ of the dermal equivalent. Data shown are the mean ±S.D. for two 8×8 $cm^2$ mesh.

FIG. 2. Development of the Extracellular Matrix of the Dermal Equivalent (A). Collagen matrix formation was evaluated by the Aniline Blue Assay (O.D./1.21 $cm^2$). Fibronectin content was evaluated using SDS-PAGE followed by immunoblotting. The approximately 200 kD fibronectin band was scanned by densitometry. (B) Glycosaminoglycans (GAGs) were evaluated as described in Methods. A square represents a 1.21 $cm^2$ of the dermal equivalent.

Figure 3:

FIG. 3. Epidermalization of the Keratinocyte/Dermal Equivalent Co-culture. Paraffin sections of the co-culture (4 wks.) were stained by Hematoxylin and Eosin (400 x). Inset: For reference to the nylon mesh culture system, a phase contrast photograph of fibroblasts 7 days after seeding on nylon mesh. (40 x).

FIG. 4. Collagen Matrix in vitro in the Dermal Equivalent Cultures and in vivo in Human Skin. Paraffin sections were stained for collagen by the Gomori Trichrome Stain. The green color in the dermis indicated the presence of collagen in the extracellular matrix (ECM). Samples tested included (A) the dermal equivalent, (B) the dermal equivalent incubated in stratification medium (4 wks.), (C) keratinocyte/ dermal equivalent co-culture (4 wks.), (D) fetal skin, (E) neonatal skin, and (F) adult skin. (400x)

FIG. 5. Decorin in vitro in the Dermal Equivalent Cultures and in vivo in Human Skin. Paraffin sections were immunoperoxidase stained for decorin. Brown areas throughout the dermis indicated the relative quantities of decorin. Samples tested included (A) the dermal equivalent, (B) the dermal equivalent incubated in stratification medium (4 wks.), (C) keratinocyte/dermal equivalent co-culture (4 wks.), (D) fetal skin, (E) neonatal skin, and (F) adult skin. (400x)

FIG. 6. Fibronectin in vitro in the Dermal Equivalent Cultures and in vivo in Human Skin. Paraffin sections were stained by indirect immunofluorescence for fibronectin. Exposures were held constant at 1±0.1 sec. Bright yellow areas throughout the dermis indicated the relative quantities of fibronectin. Samples tested included (A) the dermal equivalent, (B) the dermal equivalent incubated in stratification medium (4 wks.), (C) keratinocyte/dermal equivalent co-culture (4 wks.), (D) fetal skin, (E) neonatal skin, and (F) adult skin. (400x)

FIG. 7. Basement Membrane Zone Macromolecules. Paraffin sections of the keratinocyte/dermal equivalent co-culture (four weeks) were stained by indirect immunofluorescence to detect (A) laminin, (B) collagen Type IV, and (C) heparin sulfate proteoglycan (HSPG) at the dermal/epidermal junction.

Figure 8:

FIG. 8. Electron Microscopy of the Basement Membrane. The dermal equivalent was co-incubated with keratinocytes for five weeks. A lamina lucida (LL) with anchoring filaments (AFT) coursing through it was adjacent to the cell membrane of the basal keratinocyte (K). Also present was a lamina densa (LD) and multiple microfibrils. (300,000x)

5. DETAILED DESCRIPTION OF THE INVENTION

The present invention is an improvement of the three-dimensional cell and tissue culture system disclosed in U.S. Pat. No. 4,721,096 and U.S. Pat. No. 5,032,508, both of which are incorporated by reference in their entirety herein. According to the improved method, cells are grown on a three-dimensional matrix while cycling the cultures between metabolically favorable and metabolically unfavorable (but noncytotoxic) conditions. For purposes of clarity of disclosure, and not by way of limitation, the detailed description of the invention is divided into the following subsections:

(i) establishment of three-dimensional stromal matrix;

(ii) inoculation of tissue-specific cells onto three-dimensional stromal matrix and maintenance of cultures; and (iii) uses of the three-dimensional culture system.

5.1. ESTABLISHMENT OF THREE-DIMENSIONAL STROMAL MATRIX

According to the present invention, stromal cells, including, but not limited to, fibroblasts, endothelial cells, pericytes, macrophages, monocytes, plasma cells, mast cells, adipocytes, chondrocytes, etc., may be seeded onto a framework composed of a biocompatible, non-living material formed into a three-dimensional structure having interstitial spaces. The framework may be of any material and/or shape that: (a) allows cells to attach to it (or can be modified to allow cells to attach to it); and (b) allows cells to grow in more than one layer. A number of different materials may be used to form the matrix, including but not limited to: nylon (polyamides), dacron (polyesters), polystyrene, polypropylene, polyacrylates, polyvinyl compounds (e.g., polyvinylchloride (PVC)), polycarbonate, polytetrafluoroethylene (PTFE; teflon), thermanox (TPX), nitrocellulose, cotton, polyglycolic acid (PGA), cat gut sutures, cellulose, gelatin, dextran, polylactic acid, etc. Any of these materials may be woven into a mesh, for example, to form the three-dimensional matrix. Certain materials, such as nylon, polystyrene, etc., are poor substrates for cellular attachment. When these materials are used as the three-dimensional support matrix, it is advisable to pre-treat the matrix prior to inoculation of stromal cells in order to enhance the attachment of stromal cells to the matrix. For example, prior to inoculation with stromal cells, nylon matrices could be treated with 0.1M acetic acid, and incubated in polylysine, FBS, and/or collagen to coat the nylon. Polystyrene could be similarly treated using sulfuric acid.

Where the three-dimensional culture is itself to be implanted in vivo, it may be preferable to use biodegradable matrices such as poly glycolic acid, catgut suture material, or gelatin, for example. Where the cultures are to be maintained for long periods of time or cryopreserved, non-degradable materials such as nylon, dacron, polystyrene, polyacrylates, polyvinyls, teflons, cotton, etc. may be preferred. A convenient nylon mesh which could be used in accordance with the invention is Nitex, a nylon filtration mesh having an average pore size of 210 µm and an average nylon fiber diameter of 90 µm (#3-210/36, Tetko, Inc., N.Y.).

The openings of the matrix should be of an appropriate size to allow the stromal cells to stretch across the openings. Maintaining actively growing stromal cells which stretch across the matrix enhances the production of growth factors which are elaborated by the stromal cells, and hence will support long term cultures. For example, if the openings are too small, the stromal cells may rapidly achieve confluence but be unable to easily exit from the mesh; trapped cells may exhibit contact inhibition and cease production of the appropriate factors necessary to support proliferation and maintain long term cultures. If the openings are too large, the stromal cells may be unable to stretch across the opening; this will also decrease stromal cell production of the appropriate factors necessary to support proliferation and maintain long term cultures. When using a mesh type of matrix, as exemplified herein, we have found that openings ranging from about 150 µm to about 220 µm will work satisfactorily. However, depending upon the three-dimensional structure and intricacy of the matrix, other sizes may work equally well. In fact, any shape or structure that allow the stromal cells to stretch and continue to replicate and grow for lengthy time periods will work in accordance with the invention.

Stromal cells comprising fibroblasts, with or without other cells and elements described below, are inoculated onto the matrix. These fibroblasts may be derived from organs, such as skin, liver, pancreas, etc. which can be obtained by biopsy (where appropriate) or upon autopsy. In fact fibroblasts can be obtained in quantity rather conveniently from any appropriate cadaver organ. As previously explained, fetal fibroblasts can be used to form a "generic" three-dimensional stromal matrix that will support the growth of a variety of different cells and/or tissues. However, a "specific" stromal matrix may be prepared by inoculating the three-dimensional matrix with fibroblasts derived from the same type of tissue to be cultured and/or from a particular individual who is later to receive the cells and/or tissues grown in culture in accordance with the three-dimensional system of the invention.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, Dnase, pronase, dispase etc. Mechanical disruption can also be accomplished by a number of methods including, but not limited to the use of grinders, blenders, sieves, homogenizers, pressure cells, or insonators to name but a few. For a review of tissue disaggregation techniques, see Freshney, *Culture of Animal Cells. A Manual of Basic Technique,* 2d Ed., A. R. Liss, Inc., New York, 1987, Ch. 9, pp. 107–126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, *Culture of Animal Cells. A Manual of Basic Techniques,* 2d Ed., A. R. Liss, Inc., New York, 1987, Ch. 11 and 12, pp. 137–168.

The isolation of fibroblasts may, for example, be carried out as follows: fresh tissue samples are thoroughly washed and minced in Hank's balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional matrix (see, Naughton et al., 1987, *J. Med.* 18(3&4):219–250). Inoculation of the three-dimensional matrix with a high concentration of stromal cells, e.g., approximately $10^6$ to $5\times10^7$ cells/ml, will result in the establishment of the three-dimensional stromal support in shorter periods of time.

In addition to fibroblasts, other cells may be added to form the three-dimensional stromal matrix required to support long term growth in culture. For example, other cells found in loose connective tissue may be inoculated onto the three-dimensional support along with fibroblasts. Such cells include but are not limited to endothelial cells, pericytes, macrophages, monocytes, plasma cells, mast cells, adipocytes, etc. These stromal cells may readily be derived from appropriate organs such as skin, liver, etc., using methods known in the art such as those discussed above. In one embodiment of the invention, stromal cells which are specialized for the particular tissue to be cultured may be added to the fibroblast stroma. For example, stromal cells of hematopoietic tissue, including but not limited to fibroblasts, endothelial cells, macrophages/monocytes, adipocytes and reticular cells, could be used to form the three-dimensional subconfluent stroma for the long term culture of bone marrow in vitro. Hematopoietic stromal cells may be readily obtained from the "buffy coat" formed in bone marrow suspensions by centrifugation at low forces, e.g., 3000× g. Stromal cells of liver may include fibroblasts, Kupffer cells, and vascular and bile duct endothelial cells. Similarly, glial cells could be used as the stroma to support the proliferation of neurological cells and tissues; glial cells for this purpose can be obtained by trypsinization or collagenase digestion of embryonic or adult brain (Ponten and Westermark, 1980, in Federof, S. Hertz, L., eds, *"Advances in Cellular Neurobiology,"* Vol. 1, New York, Academic Press, pp.209–227).

Again, where the cultured cells are to be used for transplantation or implantation in vivo it is preferable to obtain the stromal cells from the patient's own tissues. The growth of cells in the presence of the three-dimensional stromal support matrix may be further enhanced by adding to the matrix, or coating the matrix support with proteins (e.g., collagens, elastic fibers, reticular fibers) glycoproteins, glycosaminoglycans (e.g., heparin sulfate, chondroitin-4-sulfate, chondroitin-6-sulfate, dermatan sulfate, keratan sulfate, etc.), a cellular matrix, and/or other materials.

After inoculation of the stromal cells, the three-dimensional matrix should be incubated in an appropriate nutrient medium under conditions that are metabolically favorable. As used herein, the phrase "metabolically favorable conditions" refers to conditions that promote cell division. Such conditions include growth in nutrient medium at 37° C. in a 5 percent $CO_2$ incubator with greater than 90 percent humidity. Many commercially available media, such as RPMI 1640, Fisher's, Iscoves, McCoy's, Dulbecco's Modified Eagle's Medium, etc. and the like, which may or may not be supplemented with serum, may be suitable for use as nutrient medium. It is important that the three-dimensional stromal matrix be suspended or floated in the medium during the incubation period in order to maximize proliferative activity. In addition, the culture should be "fed" periodically to remove the spent medium, depopulate released cells, and add fresh medium.

Newly inoculated cultures may be allowed to grow under metabolically favorable conditions for between about 3–6 cell cycles. A cell cycle, as defined herein, is the length of time between mitoses. Then the cultures may be placed under metabolically unfavorable conditions for between about 1–2 cell cycles. As used herein, the phrase "metabolically unfavorable conditions" refers to conditions that are not cytotoxic but that do not promote cell division. Such conditions include low temperatures, for example, 4°–8° C., and/or medium deficient in one or more nutrients, including isotonic buffered solutions such as PBS, HEPES-buffered Hank's medium, saline, etc. In specific, non-limiting embodiments of the invention, metabolically unfavorable conditions result in an increase in the cell cycle time by at least about twenty percent and, preferably, by at least about 50 percent, relative to the cell cycle time in nutrient medium at 37° C., 5 percent $CO_2$ and greater than 90 percent humidity.

Thereafter, the three-dimensional stromal matrix cultures may be cycled between metabolically favorable conditions for 3–4 cell cycles and metabolically unfavorable conditions for 1–2 cell cycles until the desired level of extracellular matrix material is attained. The desired level of extracellular matrix may be dependent on the nature of the tissue to be produced. For tissues that contain a relatively large amount of extracellular matrix, such as skin, a larger number of cycles may be required than for tissues such as bone marrow, which normally contain relatively less extracellular matrix.

In a preferred, specific, non-limiting embodiment of the invention, a skin dermal equivalent may be produced as follows. Fibroblasts may be harvested and seeded onto acid-washed, serum-treated medical grade nylon mesh (8×8 cm; 100 μm interstices) in Dulbecco's Modified Eagle's Medium (DMEM) containing 10 percent fetal bovine serum (FBS; defined, Hyclone, Logan UT). After one day, the mesh cultures may be transferred to 150 mm petri dishes with 45–50 ml of fibroblast medium [DMEM containing 10 percent FBS (defined and iron-supplemented, Hyclone) and 100 μg/ml ascorbic acid (Sigma)]. The cultures may then be fed with fibroblast medium every 3–4 days until they are about 12–13 days old and then may be subjected to the following incubations: 1) PBS (45 ml) at 4°–8° C. for 3–4 days; 2) fibroblast medium [45 ml] at 37° C. for 3–5 days; 3) PBS [45 ml] at 4°–8° C. for 3–4 days; and 4) fibroblast medium [45 ml] at 37° C. for 3–5 days. The resulting dermal equivalent, which is about 28–33 days old, may then either be used directly, inoculated with keratinocytes, or frozen at −70° C. in fibroblast medium containing 10 percent dimethyl sulfoxide. Preferably, the dermal equivalent is used within one month of freezing.

During incubation of the three-dimensional stromal support, proliferating cells may be released from the matrix. These released cells may stick to the walls of the culture vessel where they may continue to proliferate and form a confluent monolayer. This should be prevented or minimized, for example, by removal of the released cells during feeding, or by transferring the three-dimensional stromal matrix to a new culture vessel. The presence of a confluent monolayer in the vessel will "shut down" the growth of cells in the three-dimensional matrix and/or culture. Removal of the confluent monolayer or transfer of the matrix to fresh media in a new vessel will restore proliferative activity of the three-dimensional culture system. Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system. The flow rate could be adjusted to both maximize proliferation within the three-dimensional culture, and to wash out and remove cells released from the matrix, so that they will not stick to the walls of the vessel and grow to confluence. In any case, the released stromal cells can be collected and crypreserved for future use.

5.2. INOCULATION OF TISSUE-SPECIFIC CELLS ONTO THREE-DIMENSIONAL STROMAL MATRIX AND MAINTENANCE OF CULTURES

Once the three-dimensional stromal matrix has reached the appropriate degree of growth, the tissue-specific cells (parenchymal cells) which are desired to be cultured are inoculated onto the stromal matrix. A high concentration of cells in the inoculum will advantageously result in increased proliferation in culture much sooner than will low concentrations. The cells chosen for inoculation will depend upon the tissue to be cultured, which may include but is not limited to bone marrow, skin, liver, pancreas, kidney, neurological tissue, and adrenal gland, to name but a few.

For example, and not by way of limitation, a variety of epithelial cells can be cultured on the three-dimensional living stromal support. Examples of such epithelial cells include, but are not limited to, oral mucosa and gastrointestinal (G.I.) tract cells. Such epithelial cells may be isolated by enzymatic treatment of the tissue according to methods known in the art, followed by expansion of these cells in culture and application of epithelial cells to the three-dimensional stromal support cell matrix (neo-submucosa). The presence of the submucosa provides growth factors and other proteins which promote normal division and differentiation of the oral mucosa cells and the cells of the G.I. tract lining. Using this methodology other epithelial cells can be grown successfully, including nasal epithelium, respiratory tract epithelium, vaginal epithelium, and corneal epithelium.

A variety of tumors may be grown on the three-dimensional living stromal support. Examples of such tumors include but are not limited to adenocarcinoma and malignant melanoma which may be derived from primary or metastatic sites. Such cultures may be established in a manner similar to other three-dimensional epithelial cultures. Briefly, stromal cells, derived from either the patient's tumor or normal tissue or from an allogeneic source, are established on the mesh. After reaching near-confluency the stromal cells are inoculated with tumor cells. The tumor cells will continue to divide rapidly and form a three-dimensional solid tumor. Tumor cells grown in such a three-dimensional support exhibit a morphology similar to the in vivo state and express and shed surface antigens in a manner similar to that of solid tumors; malignant cells grown in monolayers do not exhibit the same degree of similarity to in vivo tumor tissue. Such a physiological growth of tumor cells allows applications in the study and development of new chemotherapeutic agents, individualized chemotherapy regimens, and mechanisms of metastasis. In addition such tumor cultures may be useful in individualized immunotherapy. In this regard experimentation with $^{51}CR$ release studies has indicated that Lak cells evoke a much more potent response against tumor cells grown in three-dimensions as compared to cells cultured in monolayer. Immune cells may be obtained from patients by traditional pheresis techniques and sensitized to the patient's own tumor cells grown in three-dimensional culture.

In general, this inoculum should include the "stem" cell (also called the "reserve" cell) for that tissue; i.e., those cells which generate new cells that will mature into the specialized cells that form the various components of the tissue.

The parenchymal or tissue-specific cells used in the inoculum may be obtained from cell suspensions prepared by disaggregating the desired tissue using standard techniques described for obtaining stromal cells in Section 5.1 above. The entire cellular suspension itself could be used to inoculate the three-dimensional stromal support matrix. As a result, the regenerative cells contained within the homogenate will proliferate, mature, and differentiate properly on the matrix, whereas non-regenerative cells will not. Alternatively, particular cell types may be isolated from appropriate fractions of the cellular suspension using standard techniques described for fractionating stromal cells in Section 5.1 above. Where the "stem" cells or "reserve" cells can be readily isolated, these may be used to preferentially inoculate the three-dimensional stromal support. For example, when culturing bone marrow, the three-dimensional stroma may be inoculated with bone marrow cells, either fresh or derived from a cryopreserved sample. When culturing skin, the three-dimensional stroma may be inoculated with melanocytes and keratinocytes. When culturing liver, the three-dimensional stroma may be inoculated with hepatocytes. When culturing pancreas, the three-dimensional stroma may be inoculated with pancreatic endocrine cells. For a review of methods which may be utilized to obtain parenchymal cells from various tissues, see, Freshney, *Culture of Animal Cells. A Manual of Basic Technique*, 2d Ed., A. R. Liss, Inc., New York, 1987, Ch. 20, pp. 257–288.

During incubation, the three-dimensional cell culture system should be suspended or floated in the nutrient medium. Cultures should be fed with fresh media periodically. Again, care should be taken to prevent cells released from the culture from sticking to the walls of the vessel where they could proliferate and form a confluent monolayer. The release of cells from the three-dimensional culture appears to occur more readily when culturing diffuse tissues as opposed to structured tissues. For example, the three-dimensional skin culture of the invention is histologically and morphologically normal; the distinct dermal and epidermal layers do not release cells into the surrounding media. By contrast, the three-dimensional bone marrow cultures of the invention release mature non-adherent cells into the medium much the way such cells are released in marrow in vivo. As previously explained, should the released cells stick to the culture vessel and form a confluent monolayer, the proliferation of the three-dimensional culture will be "shut down". This can be avoided by removal of released cells during feeding, transfer of the three-dimensional culture to a new vessel, by agitation of the culture to prevent sticking of released cells to the vessel wall, or by the continuous flow of fresh media at a rate sufficient to replenish nutrients in the culture and remove released cells. In any case, the mature released cells could be collected and cryopreserved for future use.

Growth factors and regulatory factors need not be added to the media since these types of factors are elaborated by the three-dimensional stromal cells. However, the addition of such factors, or the inoculation of other specialized cells may be used to enhance, alter or modulate proliferation and cell maturation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation and may be used according to the invention include prostaglandins, interleukins, and naturally-occurring chalones. Furthermore, it may be desirable to add nutrient supplements such as hydrocortisone, ascorbate, lipids, amino acids, etc. to the culture medium.

In a specific, non-limiting embodiment of the invention, a dermal equivalent produced as set forth Supra or, as described in Section 6.1.1, infra, may be inoculated with keratinocytes as follows. Fresh dermal equivalent cultures, or dermal equivalent cultures removed from the freezer and rinsed with PBS in order to remove dimethyl sulfoxide (DMSO), may be allowed to equilibrate in stratification medium [DMEM with 5 percent fetal bovine serum; 100 µg/ml ascorbate (Sigma) and 0.5 µg/ml hydrocortisone (Sigma)] for about 24–48 hours. Keratinocytes may then be seeded onto the dermal equivalent at a density of about $5 \times 10^5$ keratinocytes per cm$^2$ of dermal equivalent. The keratinocyte/dermal equivalent co-cultures may then be incubated submerged in stratification medium for 5–7 days, then raised such that keratinocytes may differentiate at the air/liquid interface. After about 12–14 days in culture, a cholesterol-rich lipid supplement (Sigma) (0.5%) may be added to the stratification medium and the cultures may be grown for an additional 12–21 days until a multi-layered stratum corneum is formed.

5.3. USES OF THE THREE-DIMENSIONAL CULTURE SYSTEM

The three-dimensional culture system of the invention can be used in a variety of applications. These include but are not limited to transplantation or implantation of either the cultured cells obtained from the matrix, or the cultured matrix itself in vivo; screening cytotoxic compounds, allergens, growth/regulatory factors, pharmaceutical compounds, etc., in vitro; elucidating the mechanism of certain diseases; studying the mechanism by which drugs and/or growth factors operate; diagnosing and monitoring cancer in a patient; gene therapy; and the production of biologically active products, to name but a few.

For transplantation or implantation in vivo, either the cells obtained from the culture or the entire three-dimensional culture could be implanted, depending upon the type of tissue involved. For example, three-dimensional bone marrow cultures can be maintained in vitro for long periods; the cells isolated from these cultures can be used in transplantation or the entire culture may be implanted. By contrast, in skin cultures, the entire three-dimensional culture can be grafted in vivo for treating burn victims, skin ulcerations, wounds, etc.

Three-dimensional tissue culture implants may, according to the invention, be used to replace or augment existing tissue, to introduce new or altered tissue, to modify artificial prostheses, or to join together biological tissues or structures. For example, and not by way of limitation, specific embodiments of the invention would include (i) three-dimensional bone marrow culture implants used to replace bone marrow destroyed during chemotherapeutic treatment; (ii) three-dimensional liver tissue implants used to augment liver function in cirrhosis patients; (iii) genetically altered cells grown in three-dimensional culture (such as three-dimensional cultures of fibroblasts which express a recombinant gene encoding insulin); (iv) hip prostheses coated with three-dimensional cultures of cartilage; (v) dental prostheses joined to a three-dimensional culture of oral mucosa.

The three-dimensional cultures may be used in vitro to screen a wide variety of compounds, such as cytotoxic compounds, growth/regulatory factors, pharmaceutical agents, etc. To this end, the cultures are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e,g., by total cell counts, and differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed. For example, drugs that increase red blood cell formation can be tested on the three-dimensional bone marrow cultures. Drugs that affect cholesterol metabolism, e.g., by lowering cholesterol production, could be tested on the three-dimensional liver system. Three-dimensional cultures of tumor cells may be used as model systems to test, for example, the efficacy of anti-tumor agents.

The three-dimensional cultures of the invention may be used as model systems for the study of physiologic or pathologic conditions. For example, in a specific embodiment of the invention, a three-dimensional culture system may be used as a model for the blood-brain barrier; such a model system can be used to study the penetration of substances through the blood-brain barrier. In an additional specific embodiment, and not by way of limitation, a three-dimensional culture of mucosal epithelium may be used as a model system to study herpesvirus or papillomavirus infection; such a model system can be used to test the efficacy of anti-viral medications.

The three-dimensional cell cultures may also be used to aid in the diagnosis and treatment of malignancies and diseases. For example, a biopsy of any tissue (e.g. bone marrow, skin, liver, etc.) may be taken from a patient suspected of having a malignancy. If the biopsy cells are cultured in the three-dimensional system of the invention, malignant cells will be clonally expanded during proliferation of the culture. This will increase the chances of detecting a malignancy and, therefore, increase the accuracy of the diagnosis. This may be especially useful in diseases such as AIDS where the infected population of cells is depleted in vivo. Moreover, the patient's culture could be used in vitro to screen cytotoxic and/or pharmaceutical compounds in order to identify those that are most efficacious; i.e. those that kill the malignant or diseased cells, yet spare the normal cells. These agents could then be used to therapeutically treat the patient.

According to the present invention, a relatively small volume of bone marrow from a diseased patient may be harvested and the patient's bone marrow destroyed by chemotherapy or radiation. The bone marrow sample may then be purged of diseased cells using an appropriate chemotherapeutic agent, expanded in vitro, and then readministered to the patient. In addition to allowing a more effective purge by treating smaller volumes of diseased marrow followed by expansion in vitro, the three-dimensional culture system can be utilized on larger volumes of purged marrow. A side effect of most purging agents is destruction and disruption of normal hematopoietic skin cells, which results in a prolonged time to engraftment and often patient mortality due to secondary infection. One effective purging agent utilized with acute nonlymphocytic leukemia is 4-hydroperoxyoyolo phosphamide (4HC) which causes a two log kill of malignant cells. In traditional treatment, 500 ml–1000 ml of diseased marrow is treated by incubation of the marrow ex vivo with 60–100 ng of 4HC/ml. Marrow is then cryopreseved and reinfused into the patient after 2–3 weeks of clinical chemotherapy. According to the present invention, a comparable volume of bone marrow may be harvested, purged with 4HC, and then expanded in vitro in three-dimensional culture, thereby allowing a more rapid engraftment time and a decrease in patient mortality.

In vitro methodologies have been useful in reducing rejection of cells used for transplantation in both animals (bone marrow transplantation in mice) and humans (allogeneic epidermal grafts). The three-dimensional bone marrow culture can be further used to promote a tolerance of cells to foreign antigens. In this regard donor hematopoietic cells may be grown in three-dimensional stromal cells from the recipient. Such cultures may be grown in the presence of three-dimensional thymic cultures which provide additional growth factors and differentiation factors which will induce maturation of lymphocytes in the bone marrow system. As the hematopoietic cells replicate and mature they will be educated to see the recipient cell antigens as "self", thereby can be come tolerant to these "foreign" cells.

Depending upon the intended use for the proliferated cells and tissue, various specialized cells may be added to the three-dimensional culture. For example, the long term growth of bone marrow cells in the three-dimensional cultures may be enhanced by the addition of certain mononuclear cell populations to the cultures by the addition of growth factors to the culture medium, or by the use of stromal cells manipulated so as to produce a desired growth factor or factors. Cells collected from these cultures may be used for transfusion transplantation and banking. The addition of lymphocytes derived from a patient to three-dimensional skin cultures may assist in evaluating and diagnosing immunological disorders, such as certain autoimmune diseases. Similarly, the addition of lymphocytes and mast cells derived from a patient to three-dimensional skin cultures may assist in evaluating the patient's allergic response to various allergens without exposing the patient to the allergens. To this end, the three-dimensional skin culture containing the patient's lymphocytes and mast cells is exposed to various allergens. Binding of lymphocyte-generated IgE to resident mast cells, when "bridged" with the allergen to which the patient is sensitive, will result in the release of vasoactive mediators, such as histamine. The release of such mediators in culture, in response to exposure of the three-dimensional culture to an allergen could be measured and used as an indication of the patient's allergic response. This would allow allergy tests to be conducted without exposing the individual to dangerous and potentially harmful allergens. This system could similarly be used for testing cosmetics in vitro.

The three-dimensional culture system of the invention may afford a vehicle for introducing genes and gene products in vivo for use in gene therapies. For example, using recombinant DNA techniques, a gene for which a patient is deficient could be placed under the control of a viral or tissue-specific promoter. The recombinant DNA construct containing the gene could be used to transform or transfect a host cell which is cloned and then clonally expanded in the three-dimensional culture system. The three-dimensional culture which expresses the active gene product, could be implanted into an individual who is deficient for that product.

The use of the three-dimensional culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the three-dimensional cultures of the invention allow for expansion of the number of transfected cells and amplification (via cell division) of transfected cells.

Preferably, the expression control elements used should allow for the regulated expression of the gene so that the product is synthesized only when needed in vivo. The promoter chosen would depend, in part upon the type of tissue and cells cultured. Cells and tissues which are capable of secreting proteins (e.g., those characterized by abundant rough endoplasmic reticulum and golgi complex) are preferable. To this end, liver and other glandular tissues could be selected. When using liver cells, liver specific viral promoters, such as hepatitis B virus elements, could be used to introduce foreign genes into liver cells and regulate the expression of such genes. These cells could then be cultured in the three-dimensional system of the invention. Alternatively, a liver-specific promoter such as the albumin promoter could be used.

Examples of transcriptional control regions that exhibit tissue specificity which have been described and could be used, include but are not limited to: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:42S–51S); insulin gene control region which is active in pancreatic beta cells (Hanahan, 1985, *Nature* 315:115–122); immunoglobulin gene control region which is active in lymphoid cells (Grosschedl et al., 1984, *Cell* 38:647–658; Adams et al., 1985, *Nature* 318:533–538; Alexander et al., 1987, *Mol. Cell. Biol.* 7:1436–1444); albumin gene control region which is active in liver (Pinkert et al., 1987, *Genes and Devel.* 1:268–276); alpha-fetoprotein gene control region which is active in liver (Krumlauf et al., 1985, *Mol. Cell. Biol.* 5:1639–1648; Hammer et al., 1987, *Science* 235:53–518); alpha-1-antitrypsin gene control region which is active in liver (Kelsey et al., 1987, *Genes and Devel.* 1:161–171); beta-globin gene control region which is active in myeloid cells (Magram et al., 1985, *Nature* 315:338–340; Kollias et al., 1986, *Cell* 46:89–94); myelin basic protein gene control region which is active in oligodendrocyte cells in the brain (Readhead et al., 1987, *Cell* 48:703–712); myosin light chain-2 gene control region which is active in skeletal muscle (Shani, 1985, *Nature* 314:283–286); and gonadotropic releasing hormone gene control region which is active in the hypothalamus (Mason et al., 1986, *Science* 234:1372–1378).

In a further embodiment of the invention, three-dimensional cultures may be used to facilitate gene transduction. For example, and not by way of limitation, three-dimensional cultures of fibroblast stroma comprising a recombinant virus expression vector may be used to transfer the recombinant virus into cells brought into contact with the stromal matrix, thereby simulating viral transmission in vivo. The three-dimensional culture system is a more efficient way of accomplishing gene transduction than are current techniques for DNA tansfection.

In yet another embodiment of the invention, the three-dimensional culture system could be use in vitro to produce biological products in high yield. For example, a cell which naturally produces large quantities of a particular biological product (e.g., a growth factor, regulatory factor, peptide hormone, antibody, etc.), or a host cell genetically engineered to produce a foreign gene product, could be clonally expanded using the three-dimensional culture system in vitro. If the transformed cell excretes the gene product into the nutrient medium, the product may be readily isolated from the spent or conditioned medium using standard separation techniques (e.g., HPLC, column chromatography, electrophoretic techniques, to name but a few). A "bioreactor" could be devised which would take advantage of the continuous flow method for feeding the three-dimensional cultures in vitro. Essentially, as fresh media is passed through the three-dimensional culture, the gene product will be washed out of the culture along with the cells released from the culture. The gene product could be isolated (e.g., by HPLC column chromatography, electrophoresis, etc) from the outflow of spent or conditioned media.

Various sample embodiments of the invention are described in the sections below. For purposes of description only, and not by way of limitation, the three-dimensional culture system of the invention is described based upon the type of tissue and cells used in various systems. These descriptions specifically include but are not limited to bone marrow, skin, liver, and pancreas but it is expressly understood that the three-dimensional culture system can be used with other types of cells and tissues. The invention is also illustrated by way of examples, which demonstrate characteristic data generated for each system described.

6. EXAMPLE: KERATINOCYTE/DERMAL CO-CULTURE

6.1. MATERIALS AND METHODS

6.1.1. CELL CULTURE OF THE DERMAL EQUIVALENT

The three-dimensional nylon mesh culture system for fibroblasts has been described in Naughton et al., 1989, In "Alternative Methods in Toxicology," Vol. 7 Goldberg, A. M. editor. MaryAnn Liebert Inc., New York, pp. 183–189). Unless otherwise indicated, all incubations were at 37° C. in a 5% $CO_2$ incubator with >90% humidity. Fibroblasts were obtained from human neonatal foreskins by sequential trypsin and collagenase digestion and then expanded in monolayer cultures until the fourth passage. Fibroblasts were then harvested and seeded onto acid-washed, serum-treated medical grade nylon mesh (8×8 cm) (100 µm) in DMEM containing 10% Fetal Bovine Serum (FBS) (defined, Hyclone, Logan UT). After one day, the mesh cultures were transferred to 150 mm petri dishes with 45–50 ml of fibroblast medium [DMEM containing 10% Calf Serum (defined and iron-supplemented, Hyclone) and 100 µg/ml ascorbic acid (Sigma)]. The following incubation/freezing protocol was developed to decrease the ratio of fibroblasts to extracellular matrix (ECM). Cultures were fed every 3–4 days until they were 12–13 days old and then were subjected to the following incubations: 1) PBS (45 ml) at 4°–8° C. until they were 15–16 days old, 2) fibroblast medium (37° C.) until they were 19–20 days old, 3) PBS (4°–8° C.) until they were 22–23 days old, and 4) fibroblast medium (37° C.) until they were 26–27 days old. At this time, the medium was aspirated and the meshes were frozen immediately in fibroblast medium containing 10% DMSO by placing in a freezer (–70° C.). The dermal equivalent was stored frozen.

6.1.2. PREPARATION OF THE KERATINOCYTE/DERMAL EQUIVALENT CO-CULTURE

Keratinocytes were obtained by trypsin (Sigma) digestion of the epidermis of neonatal foreskins. These cells were expanded in monolayer in Keratinocyte Serum Free Medium (Gibco).

The dermal equivalent cultures were removed from the freezer, rinsed with PBS to remove DMSO and allowed to equilibrate in stratification medium [DMEM with 5% fetal bovine serum; 100 µg/ml ascorbate (Sigma) and 0.5 µg/ml hydrocortisone (Sigma)] for 24–48 hr. Keratinocytes (passage 3) were seeded onto the dermal equivalent ($5 \times 10^5$/$cm^2$). The keratinocyte/dermal equivalent co-cultures were incubated submerged in stratification medium for 5–7 days, then placed on plastic frames (fabricated for Advanced Tissue Sciences) to allow differentiation at the air/liquid interface (Prunieras et al., 1983, *J. Invest. Dermatol.* 81:28s–33s). After 12–14 total days in culture, a cholesterol-rich lipid supplement (Sigma) (0.5%) was added to the stratification medium and the cultures were grown an additional 12–21 days until a multi-layered stratum corneum was formed.

6.1.3. HISTOLOGY, IMMUNOHISTOCHEMISTRY AND IMMUNOFLUORESCENCE

To compare skin in vivo to the dermal equivalent or keratinocyte/dermal equivalent co-cultures, neonatal foreskin (from routine circumcision), adult cadaver skin (from the thigh of 39 yr. old female) (Keystone Skin Bank), and fetal skin (6 months gestation) (International Institute for the Advancement of Medicine) were obtained. For histochemistry, specimens were fixed in 10% formalin in PBS and embedded in paraffin after processing in a Histokinette Tissue Processor. For immunofluorescence, specimens were fixed in ethanol (95%) (24 hr. at 4° C.) followed by dehydrating in ethanol (100%) (24 hr. at 4° C.), clearing in xylene (8 hr. at 4° C.) and embedding in paraffin (56° C.). Specimens were cut at 7 µm, mounted on Superfrost Plus slides (Fisher), cleared in xylene, and dehydrated in a graded series of ethanol. The histological stains used were Hematoxylin and Eosin (Sigma), Gomori Trichrome Stain for collagen (Sigma) and Periodic Acid Schiff (PAS) stain for carbohydrates (EM Sciences, Gibbstown, N.J.).

The presence and localization of collagen types I and III were determined with peroxidase immunohistochemistry and of collagen type IV, fibronectin, laminin and heparin sulfate proteoglycan were determined by immunofluorescence. Antibodies to human fibronectin (#A001), laminin (#A105) and decorin (#A118) were from Telios (La Jolla, Calif.), antibodies to heparin sulfate proteoglycan (#MAB458), collagen (I) (#AB745), collagen (III) (#AB747), collagen (IV) (#MAB1910) were from Chemicon (Temecula, Calif.) and monoclonal antibody to human vitronectin was a gift of David Loskutoff (Research Institute of Scripps Clinic). Secondary antibodies were goat anti-mouse phycoerythrin (Gibco), goat anti-rabbit phycoerythrin (Sigma), and goat anti-rabbit followed by rabbit peroxidase-anti-peroxidase (PAP) (Chemicon).

All incubations were at 20° C. Control samples were incubated in parallel without the primary antibody. Some specimens were digested with enzymes to unmask the antigens prior to primary antibody addition. For collagen types I and III, slides were treated with thermolysis (Sigma) (0.2 mg/ml in PBS with $Ca^{++}/Mg^{++}$; 5 min) and for fibronectin and decorin, slides were treated with bovine testicular hyaluronidase (Sigma) (0.5 mg/ml in 0.1N sodium acetateacetic acid buffer pH 6.0; 5 min).

For immunofluorescent antibody detection, deparaffinized specimens were rehydrated and blocked with TST (0.01M Tris-Cl, pH 7.6, 0.1M NaCl, 0.1% Tween-20) containing 4% goat serum and 0.1% bovine serum albumin (BSA) (Boehringer Mannhein) (30 min). Slides were then 1) incubated with primary antisera diluted in TS (0.01M Tris-Cl, 0.1M NaCl; pH 7.6) with 1% goat serum (1–3 hr.); 2) rinsed 5 times with TST; 3) soaked in TS (10 min); 4) incubated with secondary antisera conjugated with R-phycoerythrin and $2.5 \times 10^{-4}$ mg/ml propidium iodide in TS (30 min.); 5) rinsed 5 times with TST; 6) soaked in TS (10 min.) and 7) mounted in Gelmount (Fisher). Photomicrography was on a Nikon Optiphot Epifluorescent microscope. Exposure times were held constant (1±0.1 Sec.).

Specimens were prepared for immunoperoxidase staining as above except: 1) secondary antibody was goat anti-rabbit antisera diluted in TS with 1% goat serum, 2) slides were incubated with rabbit peroxidase-antiperoxidase diluted in TS (30 min.), and 3) peroxidase activity was measured by incubating slides in TS containing 0.5 mg/ml diamonbenzidine with 0.01% $H_2O_2$ for 5 min., followed by counterstaining in Harris hematoxylin and mounting in Gelmount.

6.1.4. IMMUNOBLOT ANALYSIS FOR FIBRONECTIN

To quantify fibronectin deposition in the dermal equivalent, mesh squares were extracted into TST containing 4M Urea. This extract was separated on mini SDS-PAGE gradient gels (8–15%; Jule, Inc., New Haven, Conn.) and transferred to nitrocellulose (Hoeffer) according to the method of Towbin et al., 1979, *Proc. Natl. Acad. Sci. USA*. 76:4350–4354. The nitrocellulose sheet was blocked with TST, then incubated with a 1:500 dilution of a monoclonal antibody to human fibronectin (Telios). The antibody was visualized with a standard biotin-alkaline phosphatase detection system (Pierce). The 200 Kd bands corresponding to fibronectin were scanned with a Shimadzu densitometer.

6.1.5. ANILINE BLUE ASSAY, MTT ASSAY, AND NUCLEAR COUNTS

The MTT viability assay for fibroblasts on nylon mesh is described in Triglia et al., 1991, In *"Alternative Methods in Toxicology"* Vol. 8. Goldberg, A. M. editor. MaryAnn Liebert Inc., New York, pp. 351–362. The dye, which is reduced by mitochondria to an insoluble formazan, was used as an indicator of fibroblast cell number.

The Aniline Blue Assay for net collagen matrix deposition uses aniline blue dye of Masson's Trichrome Stain (Sigma) to stain mature collagen bundles in 1.21 $cm^2$ pieces of dermal model cultures. Briefly, cultures were washed (1% Triton X-100 in PBS), formalin-fixed and stained with aniline blue dye (diluted 1:1 in $H_2O$). The dye was extracted into 95% ethanol and read at 595 nm in a microtitre plate reader (Molecular Devices Menlo Park, Calif.)

For glycosaminoglycan analysis, samples of mesh (25.4 $cm^2$) were minced and placed in Versene Buffer (0.05M sodium acetate, 2 mM N-acetylcysteine, 2 mM EDTA pH 6.0) containing 0.1 ml 2× crystallized papain (Sigma #P-3125) and incubated at 60° C. for 1–2 hrs. The digest was then removed and spun in a microcentrifuge (Eppendorf 5412, 2 min). The pellet was discarded and the supernatant assayed for total glycosaminoglycans by calorimetric complexing with alcian blue 8 GX (Sigma) (Gold, 1979, *Analytical Biochem.*, 99:183–188) and sulfated glycosaminoglycans by complexing with 1,9-dimethylmethylene blue (Farndale et al., 1982, *Connective Tissue Res.* 9:247–248). For the Alcian Blue Assay, hyaluronic acid was used as a standard and for the dimethylmethylene blue assay, heparin sulfate was used as a standard.

Nuclei counts were taken from 1000× photomicrographs (3×5 in.). For each count, six photos were taken from two slides (Hematoxylin and Eosin stained 7 µm×3 in.×5 in. ), was calculated as $8 \times 10^4$ µm$^3$. Nuclei counts were expressed as cells/µm$^3$.

6.1.6. ELECTRON MICROSCOPY

Five weeks after seeding with keratinocytes, co-culture samples were fixed for electron microscopy in Karnovsky's solution (Karnovsky, 1965, *J. Cell Biol.* 27:137A–138A), post-fixed in sodium tetroxide and stained en block for an hour each in 1% aqueous phosphotungstic acid and 2% aqueous uranyl acetate (Hulmes et al., 1981, *Proc. Natl. Acad. Sci. USA*, 78:3567–3571). Specimens were then dehydrated in graded ethanol and embedded in Spurr's resin. Ultrathin sections were cut after removal of the nylon mesh by dissection under a dissecting microscope. The sections were collected on 200 mesh nickel grids and examined in a JEOL 100 CX electron microscope.

6.2. RESULTS

6.2.1. OPTIMIZATION OF THE DERMAL EQUIVALENT FOR KERATINOCYTE GROWTH

Naughton et al. (1989, In *"Alternative Methods in Toxicology,"* Vol. 7 Goldberg, A. M editor. MaryAnn Liebert Inc., New York, pp. 183–189) have shown that stromal cells (e.g. dermal fibroblasts) grown on nylon mesh, provide a support matrix for the growth and differentiation of a second cell type (e.g. keratinocytes). In the presence of ascorbic acid, fibroblasts on nylon mesh synthesized a three-dimensional dermis-like structure containing mature collagen fibers (Fleischmajer et al., 1991, *J. Invest. Derm.*

97:638–643). Keratinocytes grew faster on these collagen-rich cultures than control cultures incubated without ascorbate (Slivka et al., 1991, *Clin. Res.* 39:82). Furthermore, when the collagen-rich cultures were incubated in PBS for 3–7 days at 4° C., keratinocyte growth was doubled and differentiation was improved. Based on these results, a protocol with alternating incubations in ascorbate containing growth medium and cold PBS was developed to produce the optimal dermal equivalent for epidermalization (FIG. 1). Fibroblast viability was monitored during the 26 day growth period by mitochondrial activity (using the MTT assay). After day 8, PBS treatments kept fibroblast viability constant. Without PBS treatment, fibroblast density (cells/$\mu m^3$) was two-fold higher. Following freezing at 26 days, fibroblast viability decreased by about 50% as measured by MTT activity. The PBS treatments and cryopreservation resulted in a dermal equivalent with an increased ratio of ECM to fibroblasts.

Figure 2A:
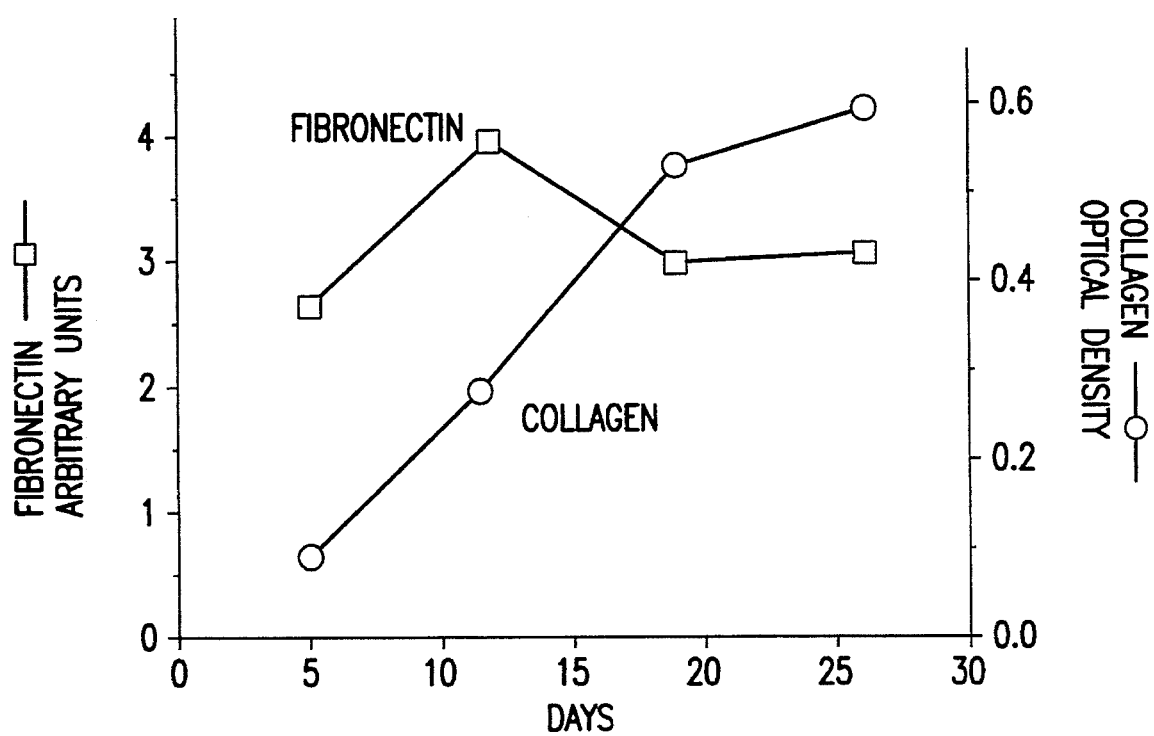
Figure 2B:
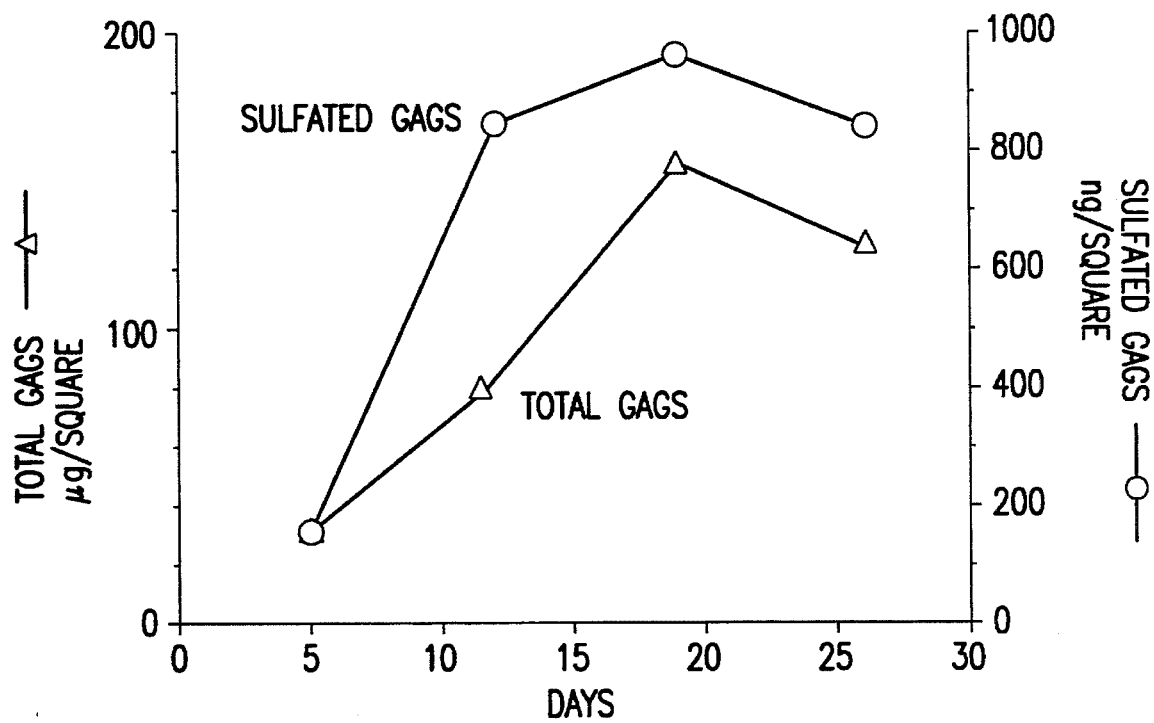

The development of the ECM of the dermal equivalent was assessed. Collagen matrix formation, as quantified by the Aniline Blue Assay, increased in a linear fashion for 26 days (FIG. 2A). In contrast, fibronectin, as estimated by immunoblotting, remained constant between days 5 and 26. Total glycosaminoglycan (GAG) content, as determined by the Alcian Blue Assay, was constant after day 19 (FIG. 2B). Sulfated glycosaminoglycan content, as determined with 1.9 dimethylmethylene blue, also increased until day 19. Sulfated GAGs represented less than one percent of the total GAGs.

This dermal equivalent supported keratinocyte growth and differentiation. After a four week incubation, a distinct basal, spinous, granular, and a multi-layered stratum corneum layer were formed in the keratinocyte/dermal equivalent co-culture (FIG. 3). The presence of fully differentiated epidermis indicated that this dermal equivalent was adequate to support epidermalization.

6.2.2. DERMAL MODEL ECM WAS SIMILAR TO FETAL/NEONATAL DERMIS ECM

The dermal equivalent was compared to fetal (6 months gestation), neonatal, and adult dermis. Human dermal development in utero is characterized by the change from high fibroblast density (1–3 months gestation) to a low density of fibroblasts relative to ECM (Holbrook, in "Biochemistry and Physiology of the Skin." Lowell A. Goldsmith, editor. Oxford University Press, New York, pp. 64–102). We found that the number of fibroblasts/$\mu m^3$ decreased five-fold during development from the fetus to neonate and another two-fold from neonate to adult (Table 1). The fibroblast density of the dermal equivalent was most similar to the neonatal dermis (Table 1, FIG. 4 A, D).

Figure 4A:
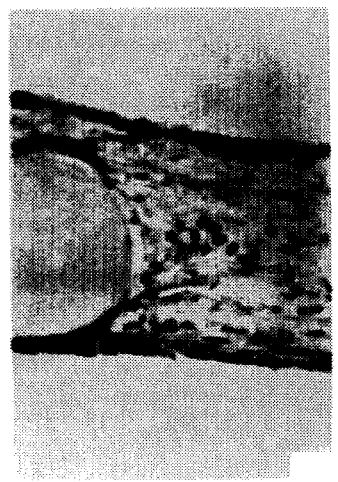
Figure 4B:
Figure 4C:
Figure 4D:
Figure 4E:
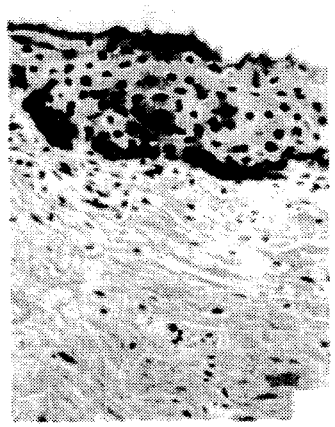
Figure 4F:

In vivo, the developing dermis begins to accumulate fibrous connective tissue (i.e. collagen) at ·3–4 months gestation and collagen fibrils and fibers increase in diameter during the third trimester (Holbrook, in "Biochemistry and Physiology of the Skin." Lowell A. Goldsmith, editor. Oxford University Press, New York, pp. 64–102). The collagen content of skin and the dermal equivalent was evaluated with the trichrome stain (FIG. 4). The intensity of trichrome staining increased from fetal (FIG. 4D) to neonatal (FIG. 4E) and from neonatal to adult dermis (FIG. 4F). Based on trichrome staining, the dermal equivalent (FIG. 4A) had a collagen content similar to fetal skin. Dermal collagen in vivo is made up of types I and III collagen (Fleischmajer et al., 1991, *J. Invest. Derm.* 97:638–643). As demonstrated by immunohistochemistry, the dermal equivalent also contained collagen types I and III (Table 1).

Figure 5A:
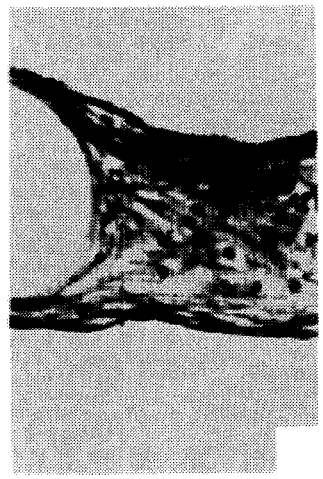
Figure 5B:
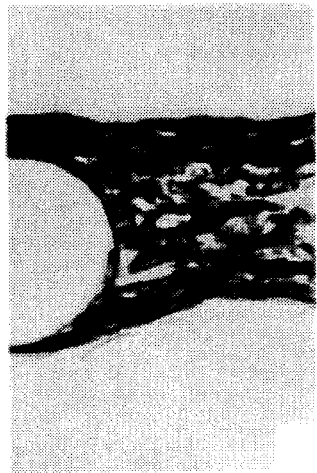
Figure 5C:
Figure 5D:
Figure 5E:
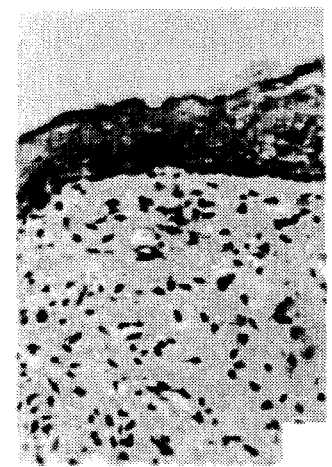
Figure 5F:

Total glycoprotein content was evaluated with the PAS stain. Very early in development, the dermis is primarily composed of glycosaminoglycans (e.g. hyaluronic acid) in a watery gel which is highly PAS positive (Holbrook, in "Biochemistry and Physiology of the Skin." Lowell A. Goldsmith, editor. Oxford University Press, New York, pp. 64–102). The dermal equivalent, like fetal dermis, was highly PAS positive and consisted of >100 $\mu$G GAGs per 1.21 $cm^2$ (FIG. 2). These GAGs were primarily non-sulfated (e.g. hyaluronic). Decorin, (a core protein of chondroitin/dermatan sulfate), was evaluated by peroxidase immunohistochemistry and found throughout the dermal equivalent (FIG. 5A) with an intensity which was similar to neonatal, fetal, and adult dermis (FIG. 5D, E, F).

Figure 6A:
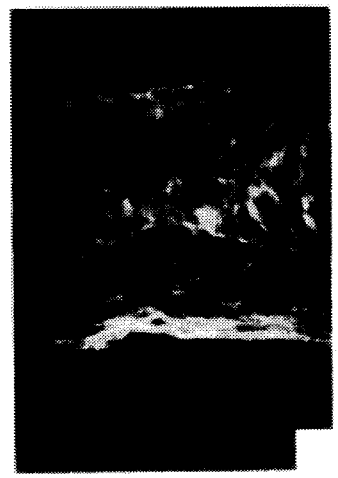
Figure 6B:
Figure 6C:
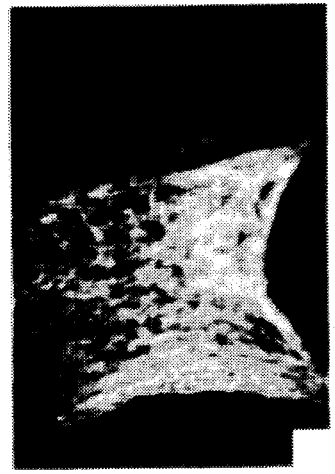
Figure 6D:
Figure 6E:
Figure 6F:
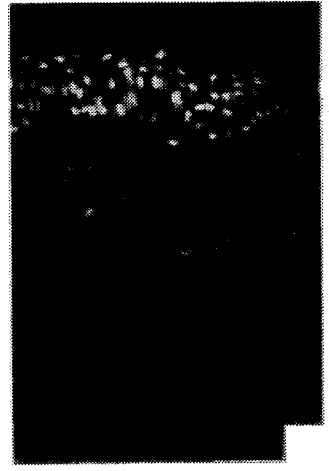

The composition of the PAS positive matrix was also examined by indirect immunofluorescence for dermal glycoproteins. Fibronectin immunofluorescence in the dermal equivalent (FIG. 6A) was similar to that of fetal dermis (FIG. 6D) and greater than that of neonatal or adult dermis (FIG. 6E, F). Laminin was not detected in the dermal equivalent at 26 days. Human vitronectin was neither detected in the dermal equivalent nor in neonatal or adult dermis except around blood vessels. Diffuse vitronectin staining was observed in fetal dermis.

6.2.3. KERATINOCYTES MODULATE DERMAL EQUIVALENT ECM

To evaluate the effect of keratinocytes on dermal ECM, the dermal equivalent was seeded with keratinocytes and the keratinocyte/dermal equivalent co-culture was grown in stratification medium for four weeks; controls for these experiments were dermal equivalent cultures maintained in the same medium for four weeks without keratinocytes. Fibronectin immunofluorescence throughout the ECM of the keratinocyte/dermal equivalent co-culture (FIG. 6C) was increased as compared to the dermal equivalent maintained in the absence of keratinocytes (FIG. 6B). When the epidermis was mechanically removed from the co-culture, human fibronectin immunofluorescence decreased as compared to controls over a 7–14 day incubation, suggesting that this effect was reversible. In contrast to fibronectin, keratinocytes had no significant effect on decorin deposition in the ECM (FIG. 5B, C) or collagen density as measured by trichrome stain (FIG. 4B, C), immunohistochemistry (Table I), or aniline blue staining, suggesting that the keratinocytes specifically increased fibronectin deposition without increasing total ECM.

Reconstitution of a functional basement membrane zone is essential for wound healing. Macromolecules essential to basement membrane formation were evaluated by indirect immunofluorescence (FIG. 7). In the four week keratinocyte/dermal equivalent co-culture, a basement membrane zone rich in collagen type IV, heparin sulfate proteoglycan, and laminin was observed. These molecules were either not detectable or in very low concentrations when control cultures were incubated in the absence of keratinocytes (Table I).

Electron microscopy was performed to determine if the molecules of the basement membrane zone were organized into a structural basement membrane. Electron microscopic evaluation of the keratinocyte/dermal equivalent co-culture showed the presence of a structural basement membrane at the dermal-epidermal junction (FIG. 8). The basement membrane consisted of a lamina lucida (LL) and lamina densa (LD). Coursing through the basement membrane were multiple microfibrils measuring approximately 10 nm in diameter.

6.3. DISCUSSION

We have optimized the growth of a novel dermal equivalent (FIGS. 1, 2) to produce a fibroblast ECM which supports complete epidermalization (FIG. 3). The ECM of this model was compared to that of fetal, neonatal, and adult human dermis (FIGS. 4, 5, 6). Matrix macromolecules present included collagen types I and III (Table I), fibronectin, and decorin in quantities similar to fetal skin (6 months gestational age). The matrix was rich in non-sulfated glycosaminoglycans (e.g. hyaluronic acid). The fibroblast density was similar to that of neonatal dermis. Overall, the dermal equivalent system closely resembled fetal/neonatal dermis in vivo.

Numerous studies have shown that the dermis controls epidermal differentiation (Holbrook, in "*Biochemistry and Physiology of the Skin*." Lowell A. Goldsmith, editor. Oxford University Press, New York, pp. 64–102). Our preliminary experiments showed that matrix composition (e.g. collagen content, fibroblast density) controlled the mitotic activity of the keratinocytes and their ability to form differentiated cell layers. The optimized dermal equivalent supported keratinocyte differentiation into an epidermis with basal, spinous, granular, and stratum corneum layers (FIG. 3). This epidermis also expressed biochemical differentiation markers such as K1 (67 Kd keratin), involucrin, filaggrin and ceramide lipids of a fully differentiated epidermis and had a selective permeability barrier. The dermal equivalent which was optimal for keratinocyte growth and differentiation was more similar in macromolecular composition to fetal and neonatal than adult dermis; it is unlikely that this was coincidental.

The growth of the dermal equivalent resembles dermis formation in vivo. At 1–2 months gestational age, the dermis of the human fetus consists of stellate, mesenchymal cells joined by cellular processes in a matrix of a watery gel of PAS-positive material (Holbrook, in "*Biochemistry and Physiology of the Skin*." Lowell A. Goldsmith, editor. Oxford University Press, New York, pp. 64–102). This dermis has a high fibroblast density as compared to adult dermis and very little collagen relative to adult dermis. During the third trimester of development, a fibrillar network of collagen bundles begins to form while cell density decreases. The dermal equivalent, during the first 12–19 days, was primarily composed of fibroblasts in an ECM rich in GAGs and fibronectin (FIG. 2). After this initial dermal development, the fibrillar network of collagen increased while the fibroblast density was maintained at neonatal levels by PBS treatments (FIG. 1). Collagen fibril formation was evaluated by electron microscopy in this system and was similar to fibril formation in vivo (Fleischmajer et al., 1991, *J. Invest. Derm.* 97:638–643). The dermal equivalent development proceeded in an order similar to dermis development in vivo.

Epidermal keratinocytes modulated the ECM composition of the dermal equivalent. In the presence of neonatal human keratinocytes, net human fibronectin deposition in the ECM was increased (FIG. 6). Since decorin and collagen content were not increased (FIG. 5), this effect may represent signalling by the differentiating epidermis to the dermis to increase fibronectin deposition.

Fibronectin is a major component of the dermis during wound healing in vivo. (Grinnel et al., 1981, *J. Invest. Derm.* 76: 181–189). Early deposition of fibronectin distinguishes fetal from adult wound healing and may be responsible of the lack of scarring observed during fetal wound healing. Longaker et al. 1989, *J. of Ped. Surgery*. 24: 799–805. Fibronectin helps provide a provisional matrix for keratinocyte migration during wound healing (Clark et al. 1982, *J. Invest. Derm.* 79: 264–269) and enhances thymidine incorporation and spreading by keratinocytes in the absence of growth factors (Woodley et al. 1990, *J. Invest. Derm.* 94: 139–143). The increased fibronectin deposition that occurs during epidermalization of the keratinocyte/dermal equivalent co-culture thus simulates wound healing. Previous workers have attributed increased fibronectin in wounds to the deposition of fibronectin around fibrin. The source of this fibronectin is thought to be primarily plasma and platelets. In contrast, our studies indicate that during wound healing keratinocytes may instruct the fibroblasts to synthesize fibronectin and thereby promote epidermalization. The dermal equivalent incorporated 3-fold more [$^3$H]-proline into fibronectin when keratinocytes were present.

During wound healing, the disrupted basement membrane zone must be reformed. Both keratinocytes and fibroblasts have been shown to secrete basement membrane zone macromolecules. When grown on collagen gels without fibroblasts, keratinocytes synthesized and secreted laminin, collagen type IV, and heparin sulfate proteoglycan into a functional zone but did not form a structural basement membrane (Schafer et al. 1991, *Exp. Cell Res.* 195: 443–457). Human dermal fibroblasts also synthesized and secreted laminin (Woodley et al. 1988, *J. Invest. Derm.* 90: 679–683). However, in the keratinocyte/dermal equivalent co-culture a basement membrane zone containing laminin, collagen type IV and heparin sulfate proteoglycan was formed (FIG. 7). These molecules were in very low abundance or were undetectable in the dermal equivalent incubated in the absence of keratinocytes (Table I). These data suggest that these molecules are either deposited by keratinocytes or synthesized and secreted by fibroblasts when co-cultured with keratinocytes.

A structural basement membrane was also formed in the keratinocyte/dermal equivalent co-culture within a period of 28 days (FIG. 8). This is remarkable since previous studies with collagen gels showed that 60 days of culture was required to produce a basement membrane zone (Hirone et al. 1979, In "*Current Problems in Dermatology*" Vol. 10. I. A. Bernstein I. A. editor. S. Karger AG, Basel pp. 159–169.) Therefore, we believe that this system provides an excellent model to study basement membrane synthesis and assembly.

In conclusion, in the keratinocyte/dermal co-culture, a tissue-like structure was formed by a sequence of events comparable to dermal development in vivo. Wound healing was simulated as keratinocytes, grew, stratified and differentiated. As this occurred, keratinocytes modulated the fibronectin composition of the ECM and macromolecules were deposited and organized into a structural basement membrane zone.

Various publications are cited herein the contents of which are hereby incorporated by reference in their entirety.

TABLE I

The Fibroblast and Matrix Composition of the in vitro Dermal Equivalent and the Keratinocyte/Dermal Equivalent Co-cultures and of in vivo Human Skin Paraffin sections were stained for collagens type I and III by immunoperoxidase immunohistochemistry and for basement membrane zone molecules collage type IV (IV), heparin sulfate proteoglycan (HSPG), and laminin (LAM) by immunofluorescence. The relative staining was assigned a value 0–4 with 4 being the most intense staining observed. Fibroblast nuclei counts were determined from histological sections as described in Methods. The DERMAL EQUIVALENT was the 26 day culture after cryopreservation. The DERMAL EQUIVALENT (+4 weeks) was the control for the CO-CULTURE. The CO-CULTURE (+4 weeks) was the keratinocyte/dermal equivalent co-culture grown for four weeks until keratinocyte differentiation was complete.

| TISSUE | FIBROBLAST DENSITY nuclei/ $8 \times 10^4$ $\mu m^3$ | COLLA-GENS I | COLLA-GENS III | BASEMENT MEMBRANE ZONE IV | BASEMENT MEMBRANE ZONE HSPG | BASEMENT MEMBRANE ZONE LAM |
|---|---|---|---|---|---|---|
| DERMAL MODEL | 11 | 4 | 2 | 0 | 0 | 0 |
| DERMAL MODEL (+4 WEEKS) | 19 | 4 | 2 | 0 | 1 | 0 |
| CO-CULTURE (+4 WEEKS) | 34 | 4 | 2 | 4 | 4 | 3 |
| FETAL | 72 | 3 | 2 | 4 | 4 | 3 |
| NEONATAL | 15 | 4 | 2 | 4 | 4 | 3 |
| ADULT | 7 | 4 | 2 | 4 | 4 | 3 |

What is claimed is:

1. An improved method of preparing a living stromal tissue in vitro that comprises stromal cells and connective tissue proteins naturally secreted by the stromal cells attached to and substantially enveloping a framework composed of a biocompatible, non-living material formed into a three-dimensional structure having interstitial spaces bridged by the stromal cells, wherein the improvement comprises:

(a) culturing the stromal cells inoculated onto the three-dimensional framework in a nutrient medium under a temperature, $CO_2$ concentration and humidity that promotes cell division, so that the inoculated stromal cells attach to the three-dimensional framework and cell division is promoted to form a three-dimensional stromal cell culture;

(b) incubating the three-dimensional stromal cell culture of step (a) in a buffer under a temperature, $CO_2$ concentration and humidity that inhibits cell division, so that cell division is inhibited yet the cells remain viable;

(c) culturing the three-dimensional stromal cell culture of step (b) in a nutrient medium under a temperature, $CO_2$ concentration and humidity that promotes cell division, so that cell division is promoted; and d) repeating steps (b) and (c) as necessary to produce extracellular matrix proteins in the three dimensional stromal culture.

2. The method of claim 1 in which the temperature that promotes cell division is 37° C.

3. The method of claim 1 in which the temperature that does not promote cell division is 4° to 8° C. and the buffer is phosphate buffered saline.

4. An improved method of preparing a living stromal tissue in vitro that comprises stromal cells and connective tissue proteins naturally secreted by the stromal cells attached to and substantially enveloping a framework composed of a biocompatible, non-living material formed into a three-dimensional structure having interstitial spaces bridged by the stromal cells, wherein the improvement comprises:

(a) culturing the stromal cells inoculated onto the three-dimensional framework in a nutrient medium under a temperature, $CO_2$ concentration and humidity that promotes cell division for 3–6 cell cycles, so that the inoculated stromal cells attach to the three-dimensional framework and cell division is promoted to form a three-dimensional stromal cell culture;

(b) incubating the three-dimensional stromal cell culture of step (a) in a buffer under a temperature, $CO_2$ concentration and humidity that inhibits cell division for 1–2 cell cycles, so that cell division is inhibited, yet the cells remain viable;

(c) culturing the three-dimensional stromal cell culture of step (b) in a nutrient medium under a temperature, $CO_2$ concentration and humidity that promotes cell division for 3–4 cell cycles, so that cell division is promoted; and (d) repeating steps (b) and (c) as necessary to produce extracellular matrix proteins in the three dimensional stromal culture.

5. The method of claim 4 in which the temperature that promotes cell division is 37° C.

6. The method of claim 4 in which the temperature that does not promote cell division is 4° to 8° C. and the buffer is phosphate buffered saline.

7. An improved method of producing a dermal equivalent which is a living stromal tissue prepared and cultured in vitro that comprises fibroblasts that have been seeded onto a framework and connective tissue proteins naturally secreted by the fibroblasts attached to and substantially enveloping the framework in which the framework is composed of a biocompatible, non-living material formed into a three-dimensional structure having interstitial spaces bridged by the fibroblasts, wherein the improvement comprises:

(a) culturing the living stromal tissue immediately after fibroblast seeding in nutrient medium at 37° C. for 12 to 13 days;

(b) culturing the living stromal tissue produced in step (a) in phosphate buffered saline at 4° to 8° C. for 3 to 4 days;

(c) culturing the living stromal tissue produced in step (b) in nutrient medium at 37° C. for 3 to 5 days;

(d) culturing the living stromal tissue produced in step (c) in phosphate buffered saline at 4° to 8° C. for 3 to 4 days; and (e) culturing the living stromal tissue produced in step (d) in nutrient medium at 37° C. for 3 to 5 days.

8. The method of claim 7 in which the nutrient medium comprises Dulbecco's Modified Eagle's Medium containing ten percent calf serum and 100 µg/ml ascorbic acid.

9. An improved method of culturing skin tissue, in which keratinocytes are grown on a dermal equivalent which is a living stromal tissue prepared and cultured in vitro that comprises fibroblasts that have been seeded onto a framework and connective tissue proteins naturally secreted by the fibroblasts attached to and substantially enveloping the framework, in which the framework is composed of a biocompatible, non-living material formed into a three-dimensional structure having interstitial spaces bridged by the fibroblasts, wherein the improvement comprises:

(a) culturing the living stromal tissue immediately after fibroblast seeding in nutrient medium at 37° C. for 12 to 13 days;

(b) culturing the living stromal tissue produced in step (a) in phosphate buffered saline at 4° to 8° C. for 3 to 4 days;

(c) culturing the living stromal tissue produced in step (b) in nutrient medium at 37° C. for 3 to 5 days, (d) culturing the living stromal tissue produced in step (c) in phosphate buffered saline at 4° to 8° C. for 3 to 4 days;

(e) culturing the living stromal tissue produced in step (d) in nutrient medium at 37° C. for 3 to 5 days;

(f) equilibrating the living stromal tissue produced in step (e) in stratification medium which is Dulbecco's Modified Eagle's Medium with 5 percent fetal bovine serum, 100 µg/ml ascorbate, and 0.5 µg/ml hydrocortisone, for 24 to 48 hours; and (g) seeding keratinocytes onto the equilibrated living stromal tissue produced in step (f) and;

(h) culturing the product of step (g) in stratification medium.

10. The method according to claim 9 in which the culture is submerged in stratification medium in step (h) and is allowed to grow for 5 to 7 days, and then is cultured at the air-liquid interface of stratification medium for about 5 to 7 days.

11. The method according to claim 10 comprising the further step of adding a cholesterol rich lipid supplement to the stratification medium and growing the culture for an additional 12 to 21 days.

12. The method of claim 11 in which the nutrient medium comprises Dulbecco's Modified Eagle's Medium containing ten percent calf serum and 100 µg/ml ascorbic acid.

13. The method of claim 10 in which the nutrient medium comprises Dulbecco's Modified Eagle's Medium containing ten percent calf serum and 100 µg/ml ascorbic acid.

14. The method of claim 9 in which the nutrient medium comprises Dulbecco's Modified Eagle's Medium containing ten percent calf serum and 100 µg/ml ascorbic acid.

* * * * *